(12) United States Patent
Gueissaz

(10) Patent No.: US 7,643,860 B2
(45) Date of Patent: Jan. 5, 2010

(54) PORTABLE INSTRUMENT FOR MEASURING A PHYSIOLOGICAL QUANTITY, INCLUDING A DEVICE FOR ILLUMINATING THE SURFACE OF AN ORGANIC TISSUE

(75) Inventor: Francois Gueissaz, Wavre (CH)

(73) Assignee: Asulab S.A., Marin (CH)

( * ) Notice: Subject to any disclaimer, the term of this patent is extended or adjusted under 35 U.S.C. 154(b) by 904 days.

(21) Appl. No.: 10/849,367

(22) Filed: May 20, 2004

(65) Prior Publication Data
US 2004/0236227 A1 Nov. 25, 2004

(30) Foreign Application Priority Data
May 21, 2003 (CH) .................................... 0904/03

(51) Int. Cl.
*A61B 5/1455* (2006.01)
(52) U.S. Cl. ...................................... 600/344; 600/310
(58) Field of Classification Search ................. 600/476, 600/443, 427, 310, 322, 344; 385/15, 31, 385/36, 129
See application file for complete search history.

(56) References Cited

U.S. PATENT DOCUMENTS

| | | | |
|---|---|---|---|
| 5,318,024 A * | 6/1994 | Kittrell et al. ................ 600/478 |
| 5,322,067 A * | 6/1994 | Prater et al. .................. 600/443 |
| 5,506,929 A | 4/1996 | Tai et al. |
| 5,551,422 A * | 9/1996 | Simonsen et al. ............ 600/322 |
| 5,610,387 A * | 3/1997 | Bard et al. ............. 235/462.44 |
| 5,713,364 A * | 2/1998 | DeBaryshe et al. .......... 600/476 |
| 5,807,261 A * | 9/1998 | Benaron et al. .............. 600/473 |
| 5,835,661 A * | 11/1998 | Tai et al. ......................... 385/36 |
| 5,997,479 A * | 12/1999 | Savord et al. ................ 600/447 |
| 6,031,954 A * | 2/2000 | Higuchi ....................... 385/120 |
| 6,452,872 B1 | 9/2002 | Teijido et al. |
| 6,690,964 B2 * | 2/2004 | Bieger et al. ................. 600/424 |
| 6,947,786 B2 * | 9/2005 | Simon et al. ................. 600/427 |
| 7,215,982 B2 * | 5/2007 | Oshima et al. ............... 600/310 |

(Continued)

FOREIGN PATENT DOCUMENTS

CN 127 80 68 12/2000

(Continued)

OTHER PUBLICATIONS

European Search Report completed Oct. 1, 2003 and English translation.

*Primary Examiner*—Eric F Winakur
(74) *Attorney, Agent, or Firm*—Griffin & Szipl, P.C.

(57) ABSTRACT

A portable instrument for measuring a physiological quantity arranged to contact with the surface of organic tissue includes, essentially arranged in the same plane: an illumination device including at least one light source with an illumination surface for subjecting a portion of organic tissue to light emission in at least one wavelength range; and a detection device distant from the illumination device for detecting intensity of light emission produced by the illumination device after propagation in the organic tissue. The illumination device includes an optical element forming a guide coupled to the at least one light source for guiding light emission from the source by total internal reflection in a substantially parallel direction to the surface of the organic tissue and for distributing light emission into several illumination zones on the surface of the organic tissue over a substantially broader area than the illumination surface of the light source.

20 Claims, 9 Drawing Sheets

U.S. PATENT DOCUMENTS

2002/0188210 A1 12/2002 Aizawa
2003/0073901 A1* 4/2003 Simon et al. ................ 600/424
2004/0171924 A1* 9/2004 Mire et al. .................. 600/407
2005/0085715 A1* 4/2005 Dukesherer et al. ......... 600/424

FOREIGN PATENT DOCUMENTS

EP          1 050 711  A1    11/2000

* cited by examiner

US 7,643,860 B2

PORTABLE INSTRUMENT FOR MEASURING A PHYSIOLOGICAL QUANTITY, INCLUDING A DEVICE FOR ILLUMINATING THE SURFACE OF AN ORGANIC TISSUE

This application claims priority from Swiss Patent Application No. 0904/03 filed May 21, 2003, the entire disclosure of which is incorporated herein by reference.

FIELD OF THE INVENTION

The present invention concerns in general a portable instrument for measuring a physiological quantity (for example the heart rhythm) arranged to be brought into contact with the surface of an organic tissue (for example skin) including, essentially disposed in a same plane, an illumination device including at least one light source of a determined illumination surface for subjecting a portion of the organic tissue to a luminous emission in at least one determined wavelength range, and a detection device remote from the illumination device for detecting the intensity of the luminous emission produced by the illumination device after propagation in the organic tissue. The present invention concerns more particularly such a measurement instrument capable of being worn on the wrist, for example in the form of an instrument having a similar configuration to a wristwatch.

BACKGROUND OF THE INVENTION

Such portable measuring instruments are already known. These portable devices are particularly employed for detecting, by optical means, the heart rhythm and/or the level of oxygen in a patient's blood. They are found in various forms ranging from clamps intended to be placed on a zone of the human body (typically on the end of a finger, on the earlobe or any other extremity of the human body sufficiently irrigated by blood) to devices worn on the wrist having a similar appearance to a wristwatch.

Within the scope of an application to measurement of the heart rhythm, the illumination device is used for generating adequate illumination of a part of the organic tissue (typically the skin) and is associated with one or several photoreceptors for detecting the intensity of the luminous emission produced by the illumination device after propagation in the organic tissue. Variations in the blood flow pulsation induce a variation in the absorption of the luminous emission produced by the illumination device, the frequency of the absorption variation essentially corresponding to the frequency of the heart pulsations. Detection of the intensity of the luminous emission after propagation in the organic tissue accompanied by adequate processing of the measurement signal or signals enables to extract an indication of the heart rhythm. The illumination devices commonly used for this type of application are relatively simple and typically consist of one or several quasi-punctual light sources. They are typically LEDs (light emitting diodes) emitting within a determined wavelength range. The detection devices commonly include one or several photoreceptors formed for example of photodiodes or phototransistors.

US Patent Application No. 2002/0188210 A1 discloses for example a portable heart rhythm detection instrument intended to be worn on the inner part of the wrist, in proximity to the wrist artery. In this example, it is proposed, in particular, to arrange several photoreceptors around a single light emitting diode. Alternatively, it is further proposed to dispose several light emitting diodes around a single photoreceptor, this alternative however being undesirable because of the increase in energy consumption and the proportional increase in manufacturing and construction costs.

In all cases, the light source or sources are, as already mentioned, quasi-punctual sources whose cone or emitting surface typically only covers an area of a few $mm^2$. This reduced emitting or illumination surface has a drawback for applications requiring illumination of an organic tissue insofar as the organic tissue has so to speak systematically localised zones where the degree of light emission absorption differs greatly from neighbouring zones. In the case of illumination of a user's skin for example, moles, hairs or other localised modifications in the epidermis can thus cause a significant variation in the light emission absorption and have a negative influence on the quality of measurement of the desired physiological quantity. Any relative movements between the measuring device and the illuminated organic tissue further add to the degradation of the measurement quality. It will be understood that these problems also arise in relation to the detection device.

It is thus desirable to illuminate the organic tissue surface more uniformly and over a larger area in order to reduce or minimise as far as possible the influence of these localised "defects" in the illuminated tissue. One solution might consist in multiplying the light sources to cover a larger area of the organic tissue. As already mentioned with reference to US document No. 2002/0188210 A1 hereinbefore, this solution is not, however essentially desirable for reasons of energy consumption and costs. It should however be noted that the increase in the number of light sources also generates connection and construction problems.

It is desirable alternatively or by way of complement, to pick up the light emission emanating from the organic tissue after propagation in the latter over a wider area in order to minimise the influence of localised defects on the signal detection quality.

It is a general object of the present invention thus to propose a portable measuring instrument for minimising the influence of localised defects in the organic tissue on the quality of illumination and/or detection of the light emission after propagation while keeping energy consumption as low as possible in order to make such a solution better suited for portable applications.

It is another object of the present invention to propose a solution whose construction remains relatively simple and whose bulkiness, particularly the thickness, remains reduced.

It is yet another object of the present invention to propose a solution which optimises as far as possible the available surface on the instrument to assure the widest possible illumination of the organic tissue and/or to assure detection of the light emission after propagation in the organic tissue over a wide area.

SUMMARY OF THE INVENTION

The present invention thus concerns an instrument for measuring a physiological quantity as mentioned hereinbefore whose features are set out in the first and second embodiments.

Additional advantageous embodiments of the present invention form the subject of embodiments modifying the first and second embodiments.

According to a first embodiment of the present invention, a portable instrument for measuring a physiological quantity arranged to be brought into contact with the surface of an organic tissue is provided and includes, essentially arranged in a same plane: (a) an illumination device including at least one light source with a determined illumination surface for subjecting a portion of organic tissue to a light emission in at least one determined wavelength range; and (b) a detection device distant from the illumination device for detecting the intensity of the light emission produced by the illumination device after propagation in the organic tissue, wherein the illumination device includes an optical element forming a guide coupled to the at least one light source for guiding the light emission from the source by total internal reflection in a substantially parallel direction to the surface of the organic tissue to be illuminated and for distributing light emission into several determined illumination zones on the surface of the organic tissue over a substantially broader area than the illumination surface of the light source. According to the solution proposed by the first embodiment, the portable measuring instrument is thus provided with an illumination device including an optical element forming a guide coupled to at least one light source for guiding the light emission of the source by total internal reflection in a direction essentially parallel to the surface of the organic tissue to be illuminated and for distributing the light emission into several determined zones of the organic tissue surface over an area substantially greater than the illumination surface of the light source.

According to a second embodiment of the present invention, a portable instrument for measuring a physiological quantity arranged to be brought into contact with the surface of an organic tissue is provided and includes, essentially arranged in a same plane: (a) an illumination device including at least one light source with a determined illumination surface for subjecting a portion of organic tissue to a light emission in at least one determined wavelength range; and (b) a detection device distant from the illumination device for detecting the intensity of the light emission produced by the illumination device after propagation in the organic tissue, wherein the detection device includes an optical element forming a guide coupled to at least one photoreceptor for picking up in several zones of the organic tissue surface the light emission produced by the illumination device after propagation in the organic tissue and for guiding the light emission by total internal reflection to the at least one photoreceptor. According to the alternative solution of the second embodiment, the detection device includes such an optical element, this time for picking up, in several zones of the organic tissue surface, the light emission produced by the illumination device after propagation in the organic tissue and for guiding this light emission by total internal reflection to at least one photoreceptor. These alternatives can advantageously be combined.

According to advantageous variants of these solutions, the optical element is configured to have a branched structure and/or an at least partially cellular structure. Preferably, the illumination zones defined by the optical illumination guide are determined so as to be at a substantially constant distance from the closest point of the geometrical contour of the detection device. If the detection device is formed of one or several quasi-punctual photoreceptors, the optical element acting as optical guide advantageously has a structure whose geometry essentially coincides with an arc of a circle or a circle of predetermined radius around the position of each photoreceptor. A structure having essentially the form of a honeycomb structure is proposed in particular.

This solution optimises as far as possible the space available to assure adequate illumination of the organic tissue. The inventor was able to observe in fact that an optical element thus structured was particularly well suited to generating the required illumination assuring optimal detection of the desired physiological quantity. This solution allows the light flux produced by the light source or sources to be channeled in a successful and optimum manner in order to illuminate the organic tissue in a number of zones arranged in a determined manner in proximity to the detection device. This solution further favours optimisation of illumination for a given energy consumption. According to the solutions of the prior art, the light flux from the light sources is not, so to speak, channeled. This results in non-optimal illumination, not only in terms of distribution, but also in terms of energy consumption, since the light emission is propagated in any direction around the source. According to the present solution, the optical element can be structured such that the light emission emerging from the optical element illuminates the organic tissue at a predetermined angle in the direction of the detection device, thus optimising still further the use of the available energy.

It will be noted in particular, that the optical illumination guide can be structured so as to assure that the light emission emanating from the illumination device is close to a vertical line relative the organic tissue to be illuminated. This advantageously enables the organic tissue to be illuminated in depth while avoiding insofar as possible direct coupling between the illumination and detection devices. According to the solutions of the prior art, the drawback of the conventional light sources (particularly LEDs) lies in the non-oriented nature of the light emission generated, the light emission thus being propagated in all directions in the organic tissue. The use of an optical guide for illuminating the organic tissue enables the light emission to be channeled so that it is propagated in depth in the tissue. The use of an optical guide for detection likewise favours detection of the light emission originating from the depths of the illuminated organic tissue, to the detriment of any light emission which is propagated at the surface of the organic tissue and which is only slightly modulated by the blood flow.

According to a particularly desirable alternative embodiment, the optical element is a solid optical guide with micro-prismatic structures. More particularly, the optical element has a first face, or lower face, directed towards the organic tissue, a second face, or upper face, opposite the first face, and lateral faces joining the first and second faces, oriented essentially perpendicularly to the surface of the organic tissue. The micro-prismatic structures are arranged on the second face and/or the lateral faces in order to redirect the light emission through the first face in the direction of the organic tissue to be illuminated or respectively to redirect the light emission emanating from the organic tissue towards the associated photoreceptor or photoreceptors.

In order to assure illumination or detection that is as uniform and homogenous as possible, the length of the micro-prismatic structures and/or their number preferably increases progressively as one moves away from the light source, respectively from the associated photoreceptor, along the optical path of the light emission. These two alternatives are applicable independently of each other or in combination and have the advantage of compensating for the decrease in intensity of the light emission produced or picked up.

Preferably, for the illumination, each micro-prismatic structure has a first facet oriented in the direction from which the light emission from the light source originates and so as to redirect the light emission in the direction of the first face of the optical element. A similar structure can be adopted for detection of the light emission emanating from the organic tissue.

The first facet at least of each micro-prismatic structure can be coated with a reflective coating in order to increase the useful light flux for illumination or detection. More widespread parts of the walls of the optical element, such as the lateral walls or the upper wall of the optical element, could be coated with a reflective coating. It should be noted that by totally coating the surface where the micro-prismatic structures are arranged, the manufacturing cost premium can be reduced a little with respect to a selective coating of the micro-prismatic structures alone, but absorption losses due to the reflective surfaces are also increased.

According to another variant, the illumination device includes first and second light sources producing light emissions in determined and distinct wavelength ranges, the optical guide being arranged to mix the light emissions from these first and second sources. The use of two distinct sources can be required in certain applications, particularly for detecting the heart rhythm or measuring the level of oxygen in the blood, where the differences in blood absorption are exploited at two distinct wavelengths. Typically, sources emitting in the red and infrared are used. Other wavelengths can also be exploited, such as yellow (approx. 590 nm) or green (approx. 480-530 nm), the choice essentially depending on the application.

One advantage of this variant lies in the fact that the optical element plays not only the role of an optical guide but also the role of an optical "mixer" for distributing light emissions in a uniform manner over the same surface along two distinct wavelengths. The prior solutions using only quasi-punctual light sources, such as LEDs, have a considerable disadvantage in this regard wherein two distinct light sources can evidently not be arranged at the same location. This necessarily results in a spatial shift between the light sources of different wavelengths and thus potentially large absorption variations between these two positions, which may have a negative influence on the detection result.

Finally, the aforementioned portable measuring instrument is perfectly suited for use in an electronic instrument worn on the wrist. The solution proposed is particularly advantageous since the optical element of the illumination device has a relatively simple construction and a small thickness allowing it to be incorporated in the bottom of the case of the instrument in proximity to the user's skin.

BRIEF DESCRIPTION OF THE DRAWINGS

Other features and advantages of the present invention will appear more clearly upon reading the following detailed description of several embodiments of the invention given solely by way of non-limiting example and illustrated by the annexed drawings, in which.

DETAILED DESCRIPTION OF THE INVENTION

Figure 1:
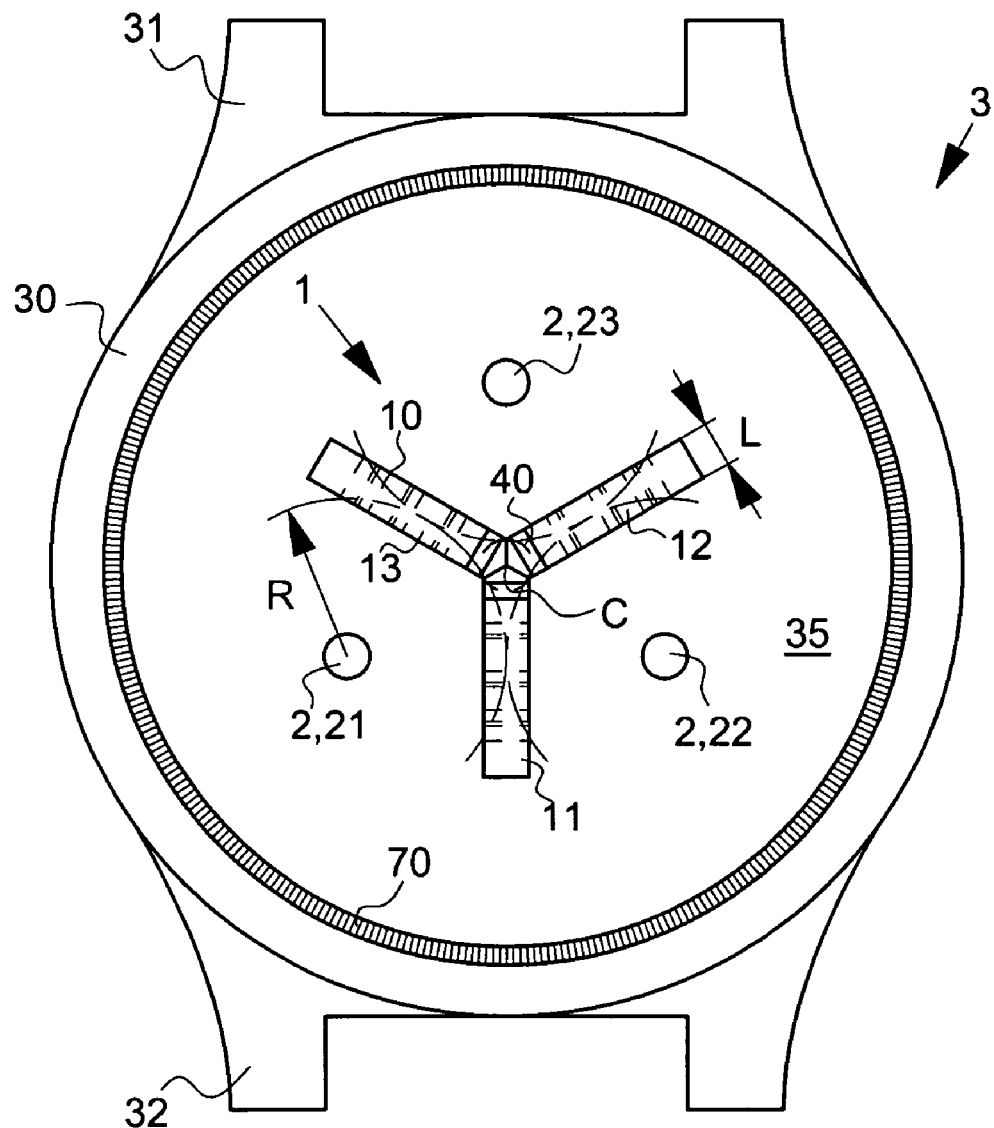
FIG. 1 shows a plan view of the bottom side of a portable electronic instrument according to one embodiment, preferably intended to be worn on the wrist, for measuring a physiological quantity and including an illumination device provided with a branched optical element and a detection device provided with three quasi-punctual photoreceptors arranged around the illumination device.

The various embodiments that will now be presented are given purely by way of illustrative and non-limiting example. In particular, it should again be stressed that the embodiments that will be presented can advantageously but not uniquely be implemented in an instrument intended to be worn on the wrist. Other portable applications of these solutions may perfectly well be envisaged.

In the embodiments illustrated in the Figures, it will be noted that a common point lies in the use of an illumination device including at least one light source coupled to a structured optical element forming a guide, this guide being structured in a determined manner as a function of geometry (in particular its periphery) and the arrangement of the detection device. As will be seen hereinafter, the detection device can also be provided with at least one optical element forming a guide coupled to at least one photoreceptor. By way of alternative, one could envisage, within the scope of the invention, providing only the detection device with such an optical guide and using one or several conventional light sources. The use of an optical guide for illumination is however preferable because of savings hoped for in terms of power consumption and distribution of the light source.

It should be noted that solutions using optical guides to assure quasi-uniform illumination of a surface are already known, typically the surface of a support bearing markings or a display. European Patent Application No. EP 1 050 711 in the name of the present Applicant discloses for example an oriented illumination device of a surface by a guide provided with micro-prismatic structures. This illumination device is used for the sole purpose of illuminating a plane surface, such as the dial of a watch, the light emission emerging from lateral faces of the guide. The use of such an illumination device in an instrument for measuring a physiological quantity for the illumination of a portion of an organic tissue is neither, however, described, nor suggested.

Within the scope of the present invention, the optical element forming a guide will preferably be a solid optical guide with micro-prismatic structures, advantageously arranged in a hollow. The material forming this guide is preferably a translucent or transparent material with a high refractive index n (typically comprised between 1.40 and 1.65) selected from among well known organic polymers which allow at least part of the light energy admitted to one end from at least one light source to be propagated by total internal reflection along the guide. Such organic polymers are for example chosen from among the acrylic polymers, particularly polymethylmethacrylate (PMMA), polycarbonate and polyesters.

It will be noted that a diffusing medium could improve the homogeneity and uniformity of illumination in the case of the use and mixing of several light sources emitting within different wavelength ranges. One can however expect more significant losses in terms of light intensity.

The optical guide could be structured by direct or indirect etching, such as mechanical machining with an appropriate tool, etching through photoresist masks, by chemical means or laser means, these techniques being cited by way of non-limiting example. It is also possible to structure the optical guide by replication from an etched die fitted to an injection machine to obtain the guides by moulding, or used for stamping a surface in which one wishes to shape the guide. Whichever technique is used, structuring can be carried out directly on the guide or on a plate with a substantially identical refractive index to that of the guide, which is subsequently applied to the actual guide, for example by bonding.

As already mentioned hereinbefore, a reflective coating can be affixed onto certain facets of the optical guide in order to increase the useful light flux for illumination of the organic tissue.

As regards the light source or sources, these will preferably be formed of quasi-punctual light sources, such as conventional light emitting diodes (LEDs) emitting within the desired wavelength range (e.g. AlGaAS diodes emitting at 650 nm or InGaN diodes emitting at 470 nm, etc.). The photoreceptor or photoreceptors of the detection device could for example be formed of photodiodes or phototransistors having an adequate response for the adopted wavelength range or ranges.

FIG. 1 schematically illustrates a first embodiment of a measuring instrument according to the invention designated as a whole by the reference numeral 3. The illumination device, designated by the reference numeral 1, includes an optical element 10 forming an optical guide coupled to a light source (at least) 40 arranged here at the centre, designated C, of the structure and which is only partially visible in FIG. 1. In the example of FIG. 1, the illumination device 1 is associated with a detection device 2 including three quasi-punctual photoreceptors 21 to 23.

The measuring instrument of FIG. 1 is for example intended for measuring the heart rhythm and its general appearance is similar to that of a wristwatch. This instrument 3 thus includes a case 30, also forming the middle part, inside which there are arranged the various electric and electronic components (not shown) of the instrument as well as a wristband (not shown) attached to case 30 in a conventional manner, for example via horns 31, 32 arranged on case 30. The illumination device 1 and detection device 2 are arranged in a back cover 35 of the watch so as to come into contact with the user's skin. FIG. 1 thus shows a plan view of the back cover side of instrument 3. Back cover 35 preferably also has a peripheral rib, designated by the reference numeral 70, the usefulness of which will be referred to more detail hereinafter.

The illumination and detection devices could alternatively be disposed on another adapted portion of the portable instrument, for example on its upper face (in this case, the user would for example have to put one of his fingers on this upper face in order to carry out the measurement of the physiological quantity concerned).

According to this first embodiment, it will be observed that the optical element 10 of illumination device 1 has a star-shaped branched structure including three substantially rectilinear branchings 11 to 13 extending essentially in the same plane along three directions displaced angularly by 120° around the centre C of the structure. The three photoreceptors 21 to 23 of detection device 2 are disposed in this example in a symmetrical configuration on the bisecting lines of the angles formed by the three branchings 11 to 13, thus along in three directions displaced angularly by 120° around structure C. Branchings 11 to 13 and photoreceptors 21 to 23 are thus all alternated every 60° approximately around the centre of the structure.

More precisely, the three photoreceptors 21 to 23 are disposed at an equal distance from centre C to form an equilateral triangle whose apex are formed by the three photoreceptors. With respect to these photoreceptors, optical element 10 is characterized by a branched geometry essentially following portions of the arc of a circle of determined radius R around the position of photoreceptors 21 to 23. The distance separating two photoreceptors is thus equal to substantially two times the radius R. Branchings 11 to 13 of the optical element also have a mean width, designated L, which is constant here, whose value is chosen to be a fraction of radius R.

The selection of the value of radius R and the value of mean width L of the branchings of the optical element are dictated by various constraints. The inventor was able to observe that the mean distance separating each photoreceptor from the neighbouring branchings should remain substantially constant. In this particular example, this distance is determined on the one hand by the value of radius R and by the value of mean width L of the branchings. Too short a distance would result in photoreceptors 21 to 23 being in too close proximity with respect to illumination device 1, preventing the light emission produced by the latter from penetrating the organic tissue sufficiently deeply and being sufficiently modulated by the variations in blood flow. Likewise, too great a distance would result in the photoreceptors being too far from illumination device 1 and would prevent detection of a signal of sufficient intensity. In practice, the inventor was able to observe that a distance of the order of less than ten millimeters was suitable.

Figure 10:
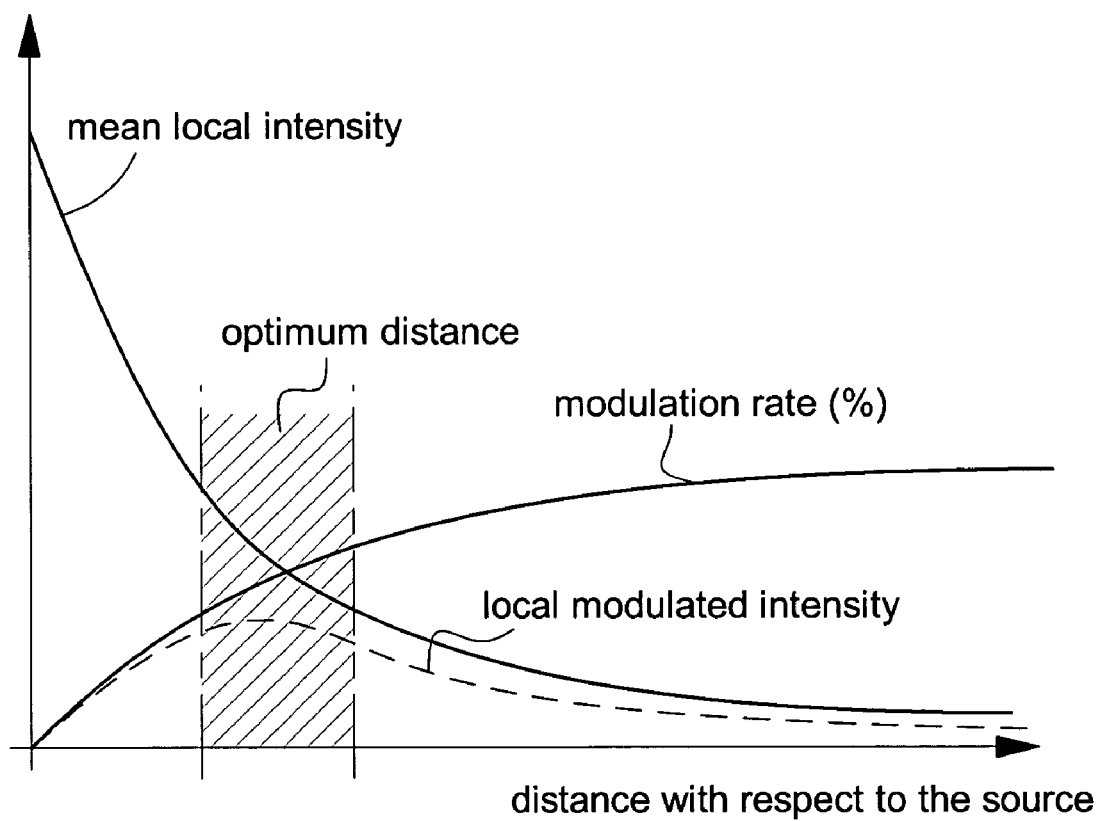
FIG. 10 shows a diagram illustrating schematically the change in the luminous intensity of a source in the organic tissue, the modulation rate of the luminous emission and the intensity resulting from modulation as a function of distance with respect to a light source.

FIG. 10 demonstrates the foregoing. It can be seen schematically here that the mean local intensity decreases almost exponentially progressively as one moves away from the source. On the other hand, the light emission modulation rate after propagation in the organic tissue (the light emission being picked up by the detection device) increases progressively as one moves away from the source typically to stabilise from a certain distance. This change is essentially linked to the fact that the farther one moves away from the source, the more deeply the light emission will have penetrated the illuminated organic tissue and the more it will be modulated by the blood flow. Stabilisation or saturation of the modulation rate results from the fact that the distribution of the blood vessels varies up to a depth determined with respect to the surface of the organic tissue from which it becomes homogenous. A longer transmission path in the organic tissue consequently no longer contributes to increase the modulation rate.

The modulated intensity which essentially results from multiplication of the aforementioned two curves (curve in dotted line in FIG. 10) thus has an amplitude peak as shown in the diagram. In order to optimise operation of the optical measuring device, an adequate spacing has thus to be selected between the illumination and detection devices that essentially coincides with this amplitude peak. This optimal distance (indicated by the hatched part in FIG. 10) varies as a function of the nature of the illuminate organic tissue and in particular of the depth at which the blood vessels are located. For use on the wrist, the inventor has determined that this distance is typically 10 mm or less.

In the case of an application to an electronic instrument worn on the wrist where the surface of the back cover in contact with the skin is typically of the order of ten $cm^2$, it will be noted that, in practice, it is possible to arrange at little less than ten "overlapped" photoreceptors in an optical guide structured as proposed.

In the example of FIG. 1, it should be observed that the distance between each photoreceptor 21 to 23 and the neighbouring branchings is not strictly constant because of the rectilinear shape of branchings 11 to 13. It should however be specified that strict respect for a constant distance between the photoreceptor and the optical guide is not in itself primordial. A certain tolerance is acceptable. It should also be specified that it is especially important to ensure that the optical guide is structured to inject and distribute the light emission from the source or sources into zones determined with respect to the positions of the photoreceptors. The optical guide itself could thus follow a geometry that does not necessarily respect a predetermined distance with respect to the geometry of the detection device.

Figure 1A:
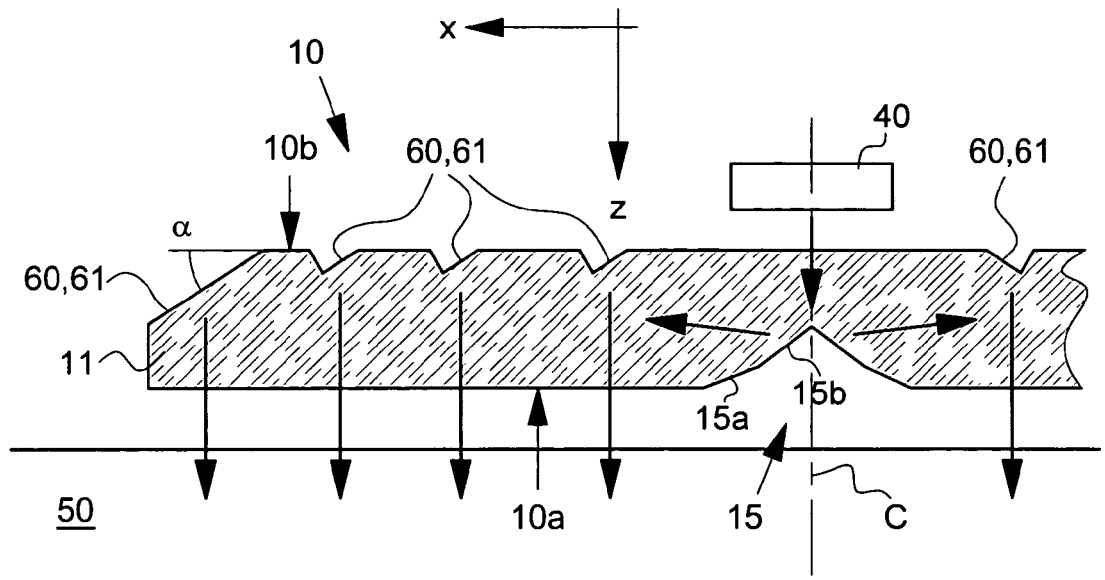
FIGS. 1a and 1b show enlarged views respectively in cross-section (along the line A-A of FIG. 1b) and a plan view of a portion of the branchings of the optical element of FIG. 1 where micro-prismatic structures are arranged on the upper face of the optical element; these views further illustrating the arrangement of the light source with respect to the optical element of the illumination device.
Figure 1B:
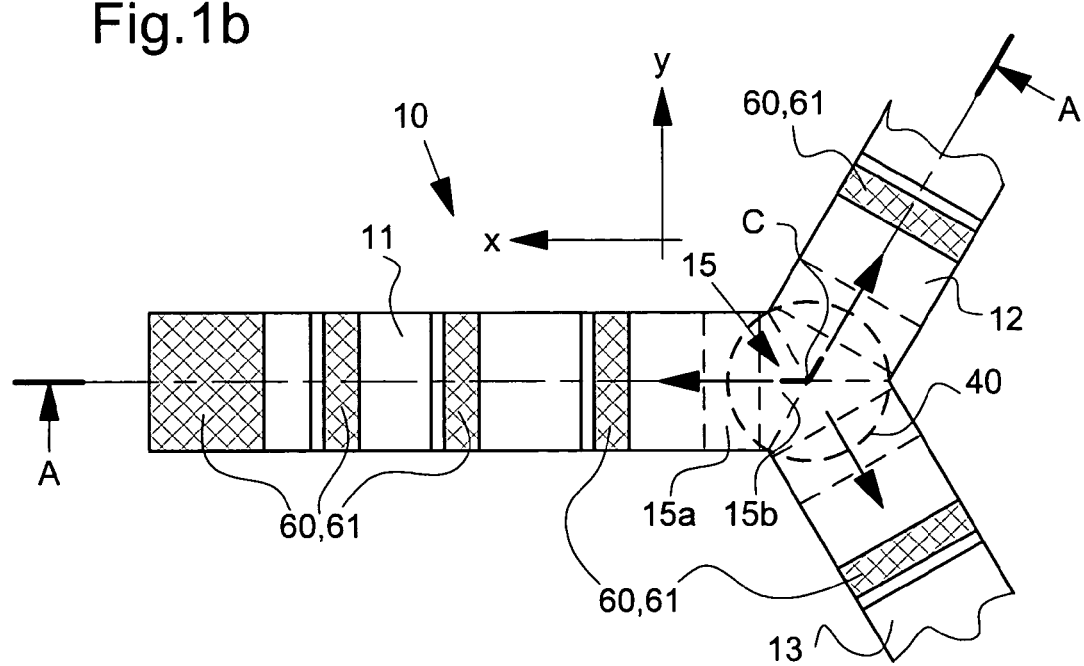

The configuration of the illumination device of FIG. 1 will now be examined more particularly, such configuration being detailed in the views of FIGS. 1a and 1b. FIG. 1b is a partial enlarged view of optical element 10 of FIG. 1 seen from the side of its upper face, designated 10b, i.e. its face opposite face 10a intended to be directed towards the surface of the organic tissue to be illuminated (50 in FIG. 1a). FIG. 1a is a partial cross-section of optical element 10 taken along the line A-A in FIG. 1b and which also illustrates the arrangement of light source 40.

For the sake of clarity, a set of Cartesian coordinates x, y, z is defined and added to each Figure to specify the orientation of the various views in space. It will be noted in particular that this set of coordinates is defined such that the general plane of optical element 10 is parallel to the x-y plane (cf. FIG. 1), branching 11 being parallel to the x axis, and that the z axis points from the bottom of the instrument towards the surface of the organic tissue to be illuminated 50 (cf. FIG. 1a).

As illustrated in FIGS. 1a and 1b, illumination device 1 includes in this example a single light source 40, preferably a light emitting diode or LED, disposed at centre C of the structure such that its light emission is oriented along the z axis towards the central portion of the optical element as indicated by the arrow. Because of its perpendicular orientation to the plane of optical element 10, facets 15a, 15b are arranged in a hollow in the lower face 10a of optical element 10. These facets 15a, 15b are oriented to redirect, via total internal reflection, the light flux from source 40 into the various branchings of the optical element. In this embodiment, these facets consequently form a recess 15 having the general appearance of a tetrahedron or, more exactly, two portions of a tetrahedron. Several facets (two in this example) whose angle decreases with respect to the x-y plane progressively as one moves away from centre C of the structure are preferably used given that the angle of incidence of the beams produced by light source 40 is generally not constant, the light rays produced by the source typically forming a cone of emission around the z axis. It will be understood that facets 15a, 15 forming recess 15 can be replaced by any other suitable geometry allowing the light emission from source 40 to be redirected into the various branchings, for example a curved profile geometry.

As illustrated in FIGS. 1a and 1b, the light emission produced by source 40 is thus redirected into each branching 11, 12, 13 of the optical element, each of these branchings including reflective zones 60 for redirecting the light flux by total internal reflection into different zones of the surface of organic tissue 50 as schematised by the arrows in FIG. 1a. In the example of FIGS. 1a and 1b, zones 60 are arranged on the upper face 10b of the optical element and are formed of at least one facet 61 inclined in the direction from which the light beam, produced by source 40, originates, to form microprismatic structures. In FIGS. 1a and 1b, four facets of this type can be seen on branching 11. Three of them are distributed over the length of branching 11 and are each formed by a V-shaped hollow portion arranged on face 10b. The fourth facet is arranged at the end of branching 11 and has here a larger area than the other three.

The angle of facets 61 with respect to the x-y plane, designated α, is determined so as to redirect a part of the incident light beams towards the organic tissue to be illuminated 50. The value of this angle α is essentially dictated by the nature of the material used (particularly the refractive index n of the material forming optical guide 10), the orientation of the incident beams in the guide as well as the nature of the external medium. As already mentioned, it is possible to envisage coating facets 61 with a reflective coating (or even the entire upper face 10b) in order to increase the light flux emerging through lower face 10a of optical element 10.

Generally, the design of the optical element has to answer a certain number of geometrical constraints. One of them is the value of the critical angle designated $\theta_c$, defined with respect to the line perpendicular to the face concerned, above which total reflection of the light beams striking the face is produced. This critical angle is commonly given by the following formula:

$$\theta_c = \arcsin\left(\frac{n_1}{n_2}\right) \quad (1)$$

where $n_1$ corresponds to the refractive index of the external medium (equal to 1 in the case of air) and $n_2$ corresponds to the refractive index of the guide where the light beams are being propagated. In order to ensure that total internal reflection of the beams always occurs inside optical guide 10, the relation according to which the light beams inside the guide have to have an angle of incidence with respect to the face concerned that is greater than the aforementioned critical angle $\theta_c$ must thus be respected. In the opposite case, a portion of the light beams will then be propagated outside the optical guide by refraction. As already mentioned, if necessary, reflective coatings allow an incident light beam to be totally reflected. This results, however, in losses by absorption, which it is preferably to minimise as far as possible.

Figure 2A:
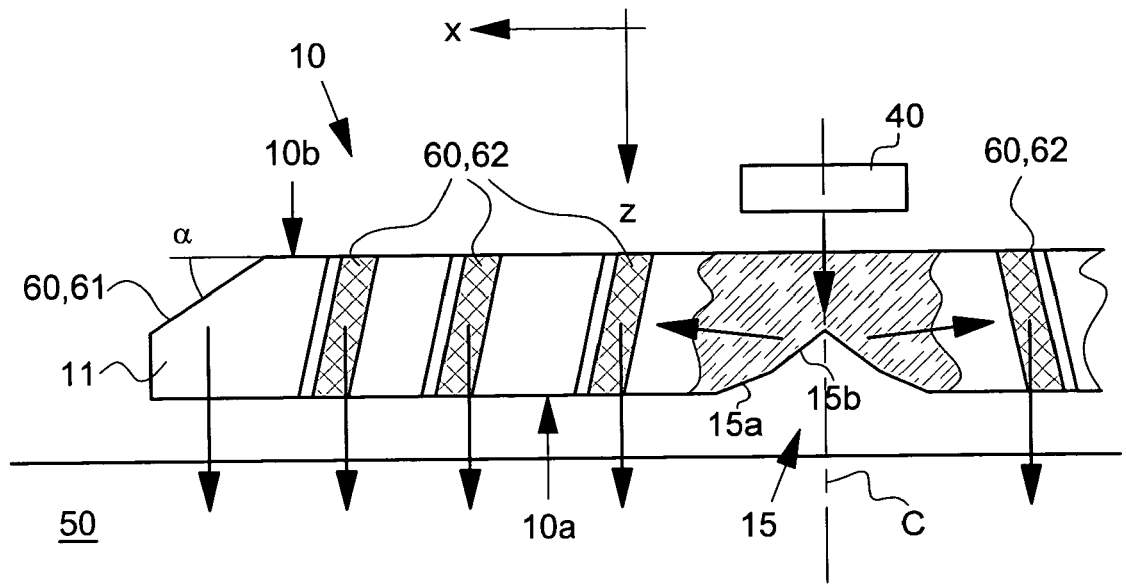
FIGS. 2a and 2b show similar views to the views of FIGS. 1a and 1b illustrating an alternative embodiment where the micro-prismatic structures are arranged in particular on the lateral walls of the branchings.
Figure 2B:
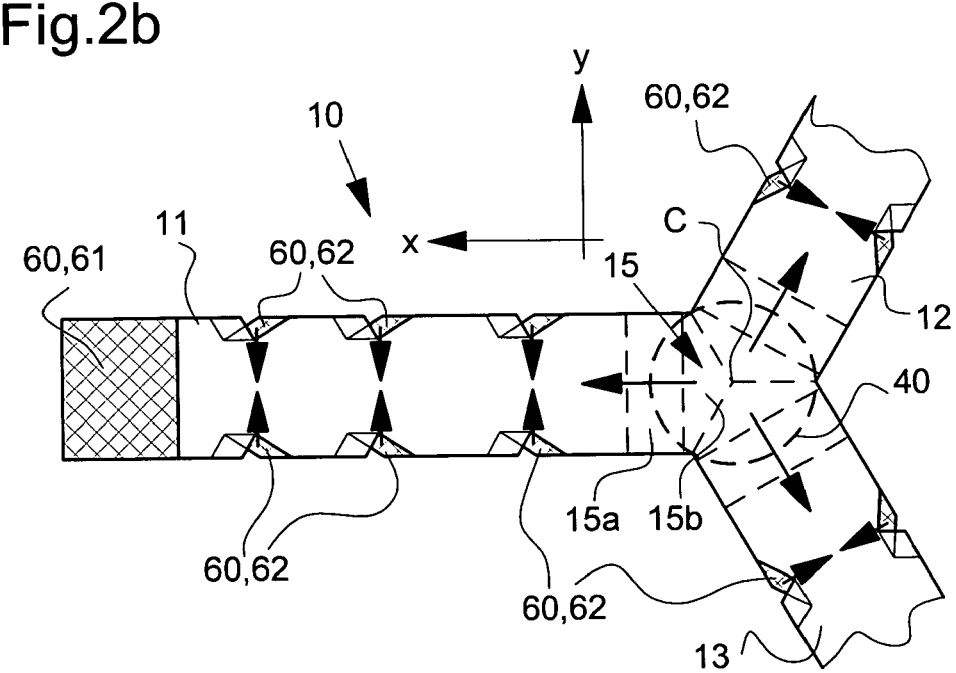

FIGS. 2a and 2b show an alternative embodiment illustrating an alternative for making reflecting zones 60. Instead of making these zones 60 on upper face 10b of optical element 10, it is thus possible to make the zones on the lateral faces of optical element 10 which are both essentially perpendicular to the surface of the organic tissue to be illuminated and parallel to the general direction of propagation of the light flux in the optical element. This could be for example faces designated 10c and 10d of branching 11 in FIGS. 2a and 2b (and the corresponding lateral faces of the two other branchings 12 and 13). In order to exploit these faces, as illustrated in FIGS. 2a and 2b, facets should be arranged, designated 62 and inclined both in the direction from which the light beam produced by source 40 originates and in the direction of the surface of the organic tissue to be illuminated. One and/or the other of faces 10c, 10d can be structured in this way. It should be noted that the light flux emerging through face 10a of the optical element that is reflected by a facet 62 will have a general direction with not only a component along the z axis, but also a component along the y axis (or even x). In the example being discussed, given that photoreceptors are arranged on either side of each of branchings 11 to 13, it is preferable to structure the two lateral faces of each branching symmetrically, in order to ensure uniform distribution illumination.

The two structuring methods discussed with reference to FIGS. 1a, 1b and 2a, 2b can advantageously be combined. Moreover, as illustrated in FIGS. 2a and 2b, the end of each branching includes an inclined facet 61 like the solution of FIGS. 1a and 1b. Further, the size of the facets (depth and/or width) and their number per surface unit can be variable. It is particularly desirable to increase the reflective surface of zones 60 and/or to increase the number progressively as one moves away from light source 40 along the propagation path of the light beam, in order to compensate, to a certain extent, for the progressive decrease in the intensity of the light flux.

Figure 3:
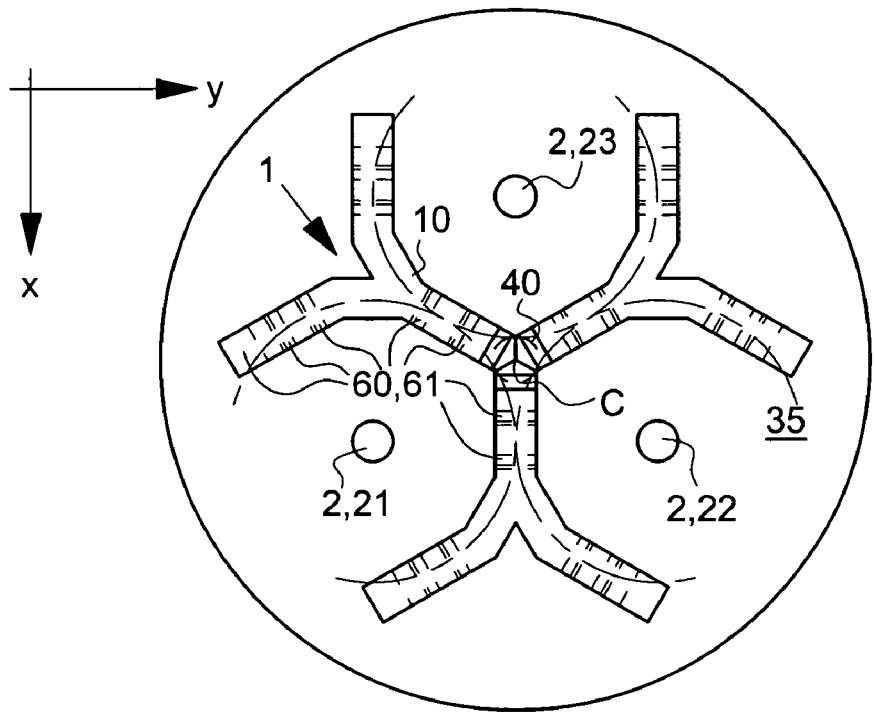
FIG. 3 is a similar plan view to the view of FIG. 1 illustrating a variant wherein the optical element has additional branchings, the branchings advantageously defining open cells around various photoreceptors.
Figure 4:
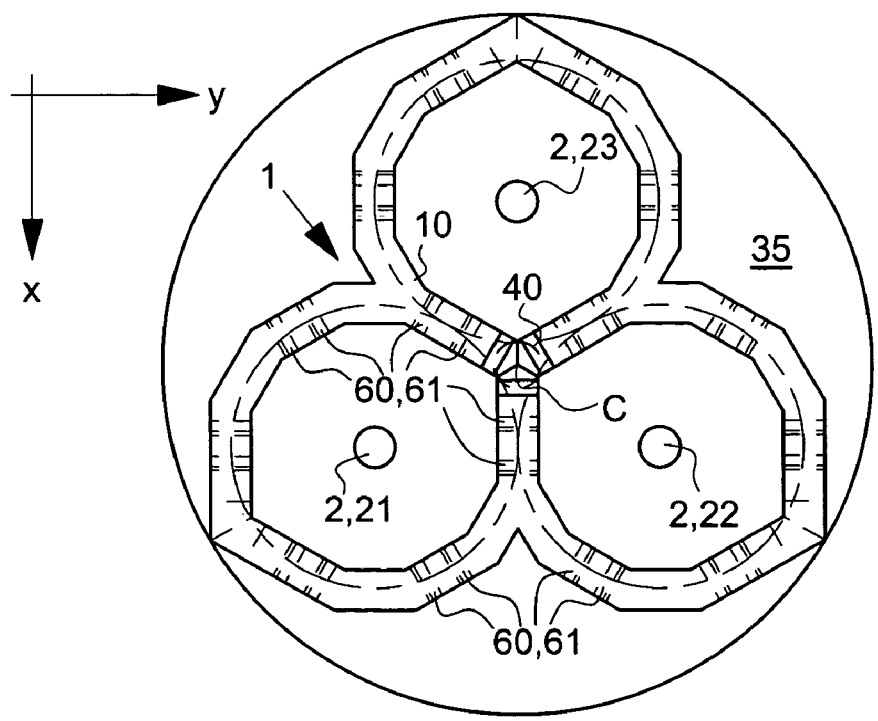
FIG. 4 illustrates yet another variant wherein the optical element has branchings defining closed cells of polygonal shape, like a honeycomb structure.

The structure of optical element 10 is evidently not limited to the single example of FIG. 1. As illustrated in FIGS. 3 and 4, optical element 10 can have a wider branched structure forming open (FIG. 3) or closed (FIG. 4) cells around the position of the various photoreceptors. In order to optimise as far as possible the available surface on the portable instrument, a honeycomb cellular structure appears particularly advantageous because of its optimum use of space. As already mentioned hereinbefore, by adopting such a configuration, it appears in practice to be possible to arrange less than ten quasi-punctual photoreceptors at the heart of a structured cellular optical element on an area of ten or so cm² such as is typically available on the back cover of an instrument worn on the wrist.

In the variants of FIGS. 3 and 4, it will be noted that reflective zones 60 of optical element 10, which allow reorientation of the light flux in the direction of the organic tissue to be illuminated have been shown like the reflective zones illustrated in FIGS. 1, 1a and 1b. These diagrams are only schematic and illustrative. In particular, structuring of this type illustrated by way of variant in FIGS. 2a and 2b can be used as a replacement or complement. Moreover, the number, shape and arrangement of the reflective zones can vary. Finally, the dimensions of the reflective zones (width and depth) are not necessarily to scale.

Figure 5:
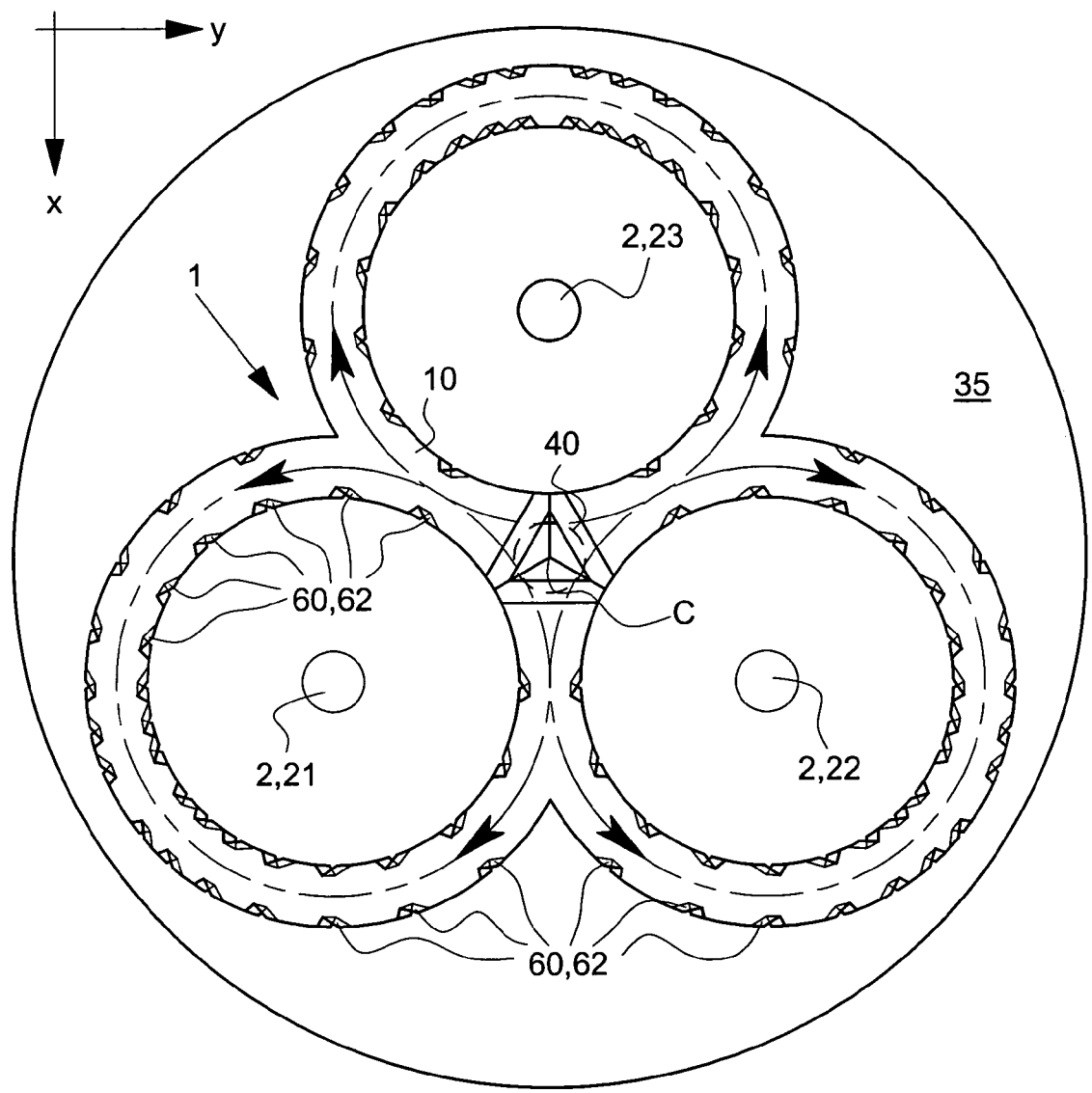
FIG. 5 illustrates a variant wherein the optical element forming a guide has a similar cellular structure to that of FIG. 4, each cell having, however, an essentially circular or annular shape.

FIG. 5 shows yet another variant, similar to that of FIG. 4, wherein the optical element has a cellular structure in which each cell has a circular or annular shape instead of the polygonal cellular structure of FIG. 4. By way of example, reflective zones 60 are structured like the zones of FIGS. 2a and 2b on the lateral faces of guide 10. In FIG. 5, the propagation path of the light beam (again produced at centre C of the structure) into the various branchings of optical element 10 is also indicated by arrows.

Figure 6:
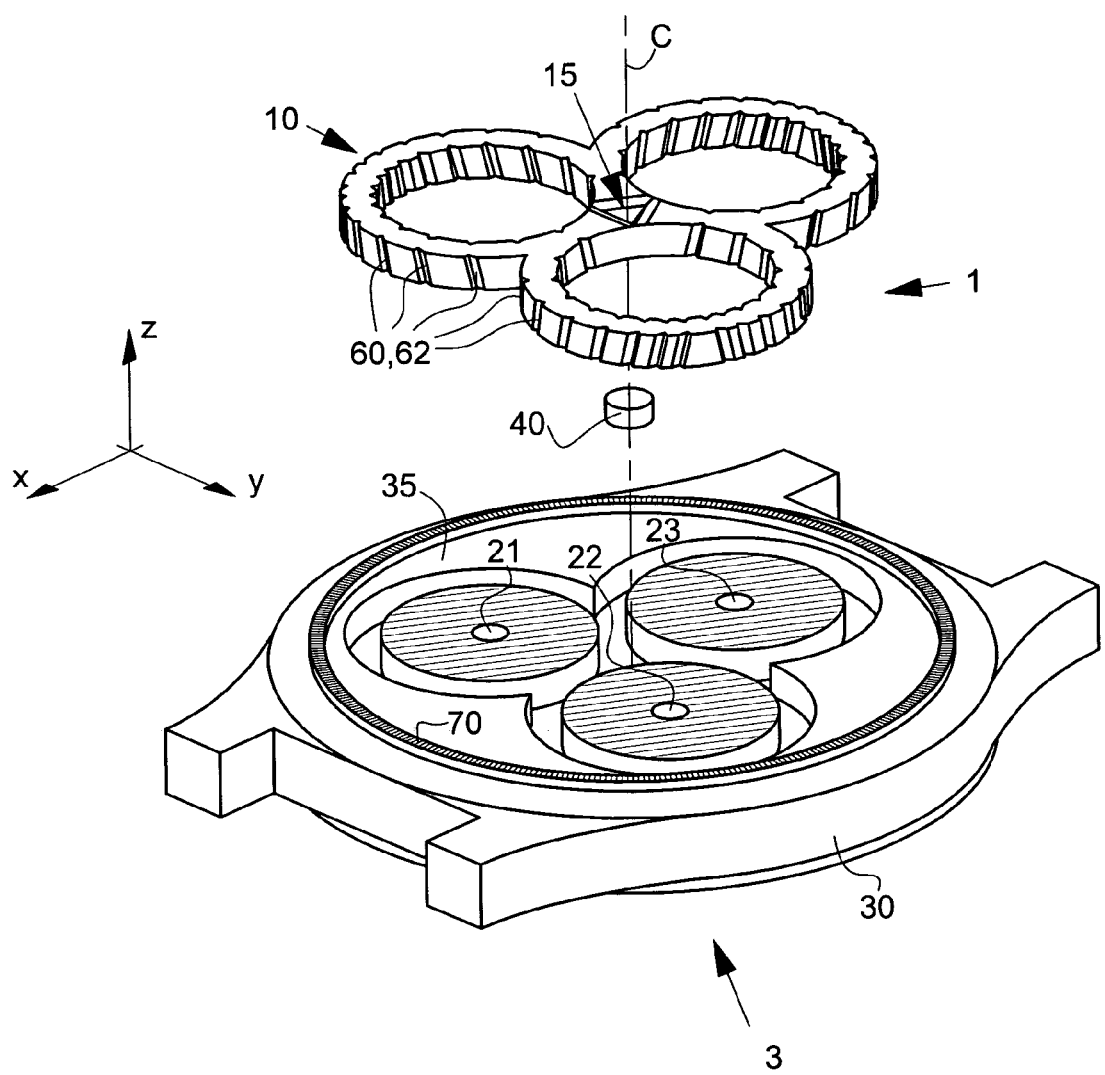
FIG. 6 is a schematic perspective view of an electronic instrument intended to be worn on the wrist and taking a similar form to that of a wristwatch, this instrument including an illumination device in accordance with the variant of FIG. 5 arranged in its bottom.

FIG. 6 is a perspective view illustrating the assembling of the illumination device shown in FIG. 5 in back cover 35 of portable instrument 3. In accordance with the foregoing description, the light emitting diode 40 is arranged, in this example, in a central area of back cover 35 and directed such that its light emission is oriented parallel to the z axis in the direction of recess 15 arranged on the lower face (the face directed upwards in FIG. 6) of optical element 10.

Spacers (not shown) can be arranged at intervals between optical element 10 and back cover 35 so as to arranged a small air space between the walls of guide 10 and the neighbouring walls of back cover 35. An intermediate wall (not shown) could also be inserted between back cover 35 and guide 10, on the one hand, and the surface of the organic tissue to be illuminated on the other hand. In this regard, as already mentioned, back cover 35 preferably has a peripheral rib 70, of annular shape here, which projects outside of the back cover in the direction of the organic tissue to be illuminated. In this configuration, the purpose of this rib 70 is essentially to answer two objectives. The first of these objectives is to form an optical barrier preventing the ambient lighting to disturb the measurement of the physiological quantity. The second of these objectives is to ensure that the optical guide is not directly in contact with the organic tissue. It is in fact preferable to ensure that a space permanently exists between the optical guide and the illuminated organic tissue so that the nature of the interface between the guide and the external environment remains constant and invariable over time, particularly during relative movements of the portable instrument with respect to the organic tissue.

In the illustration of FIG. 6, it will be noted that rib 70 could advantageously follow the external contour of illumination device 1, in which case, this rib 70 would have a shape with three lobes rather than annular as illustrated. However, ribs could advantageously be inserted between the illumination and detection devices to limit direct light coupling between the devices.

In addition to the presence of rib 70, it is also preferable to arranged the surfaces of back cover 35, which are located between the illumination and detection devices (the three hatched annular surfaces in FIG. 6) such that they do not reflect the light emission produced by the illumination device. Indeed, insofar as a space exists between back cover 35 and the organic tissue on which it lies, a portion of the light emission could be reflected between the surface of back cover 35 and the surface of the illuminated organic tissue before being picked up by the detection device. By arranging an anti-reflective coating on the intermediate surfaces of back cover 35, between the illumination and detection devices, the disturbing influence of these multiple reflections between the back cover and the organic tissue will be limited.

Figure 7:
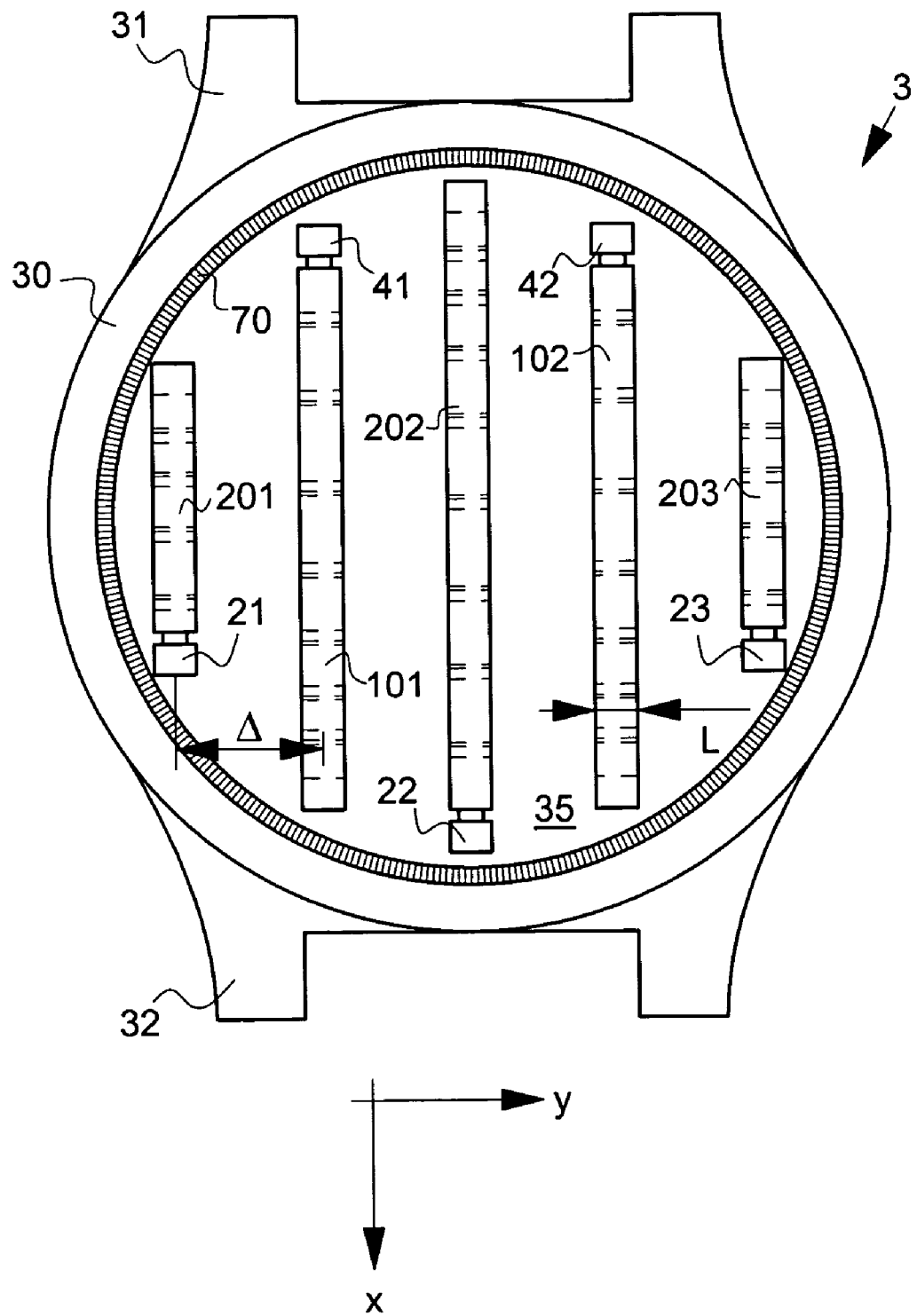
FIG. 7 illustrates a variant wherein the illumination device includes two distinct optical guides for illuminating the surface of the organic tissue and wherein the detection device itself is provided with optical guides for picking up the light emission after propagation in the organic tissue, each optical element forming a guide having here the shape of an essentially rectilinear bar.

FIG. 7 shows yet another variant, which illustrates several modifications that can be envisaged within the scope of the present invention.

First of all, the embodiments presented hereinbefore only include a single optical element forming a guide coupled to a single light source. It is perfectly possible to envisage using several distinct optical guides each coupled to one or several light sources. FIG. 7 shows, for example, a variant including two optical guides 101 and 102, of essentially rectilinear shape, each coupled to a light source 41, 42.

Secondly, the arrangement of the light source with respect to the optical guide to which it is coupled can take different configurations. FIG. 7 shows, for example, that each light source 41, 42 is placed facing one end of the associated optical guide, the light emission being oriented along the x axis in this example. This solution thus does not require an optical device to redirect the light beams in the general plane of the guide as in the embodiments of FIGS. 1 to 6.

Thirdly, the detection device can advantageously also be itself provided with one or several optical elements forming a guide to pick up the light emission propagated in different zones of the surface of the organic tissue being examined, each optical element being coupled to at least one photoreceptor. In FIG. 7, this illustrated by the presence of three optical elements 201, 202, 203 forming guides arranged alternately on either side of optical illumination elements 101, 102 and each coupled, via one of their ends, to a photoreceptor 21, 22, respectively 23. The structuring of these optical elements is essentially similar to that of the optical illumination guides presented hereinbefore.

Fourthly, the geometry of the guide does not necessarily have to follow the arcs of a circle as in the preceding embodiments. The arc of a circle shape is essentially dictated by the quasi-punctual or the photoreceptor(s) used in the embodiments of FIGS. 1 to 6. The essential lies above all in respecting a determined distance, within a given tolerance range, between the zones where the illumination device injects the light beam and the zones where the detection device picks up the light beam after propagation in the organic tissue.

On this last point, it should be noted that the use of one or several optical guides for picking up the light emission after propagation in the organic tissue opens up other configuration possibilities. In FIG. 7, it can thus be seen that the use of optical guides for the detection of the light emission enables the illumination and detection devices to be configured in a particularly simple manner, geometrically speaking. Indeed, the various optical guides used 101, 102, 201, 202 and 203 have here simply the form of a structured rectilinear bar, that is thus particularly easy to manufacture. Care will be taken in such case to respect a certain spacing A between the optical elements and a certain width L of the optical elements, this spacing A and width L being, however, able to vary from one optical guide to another.

Figure 8:
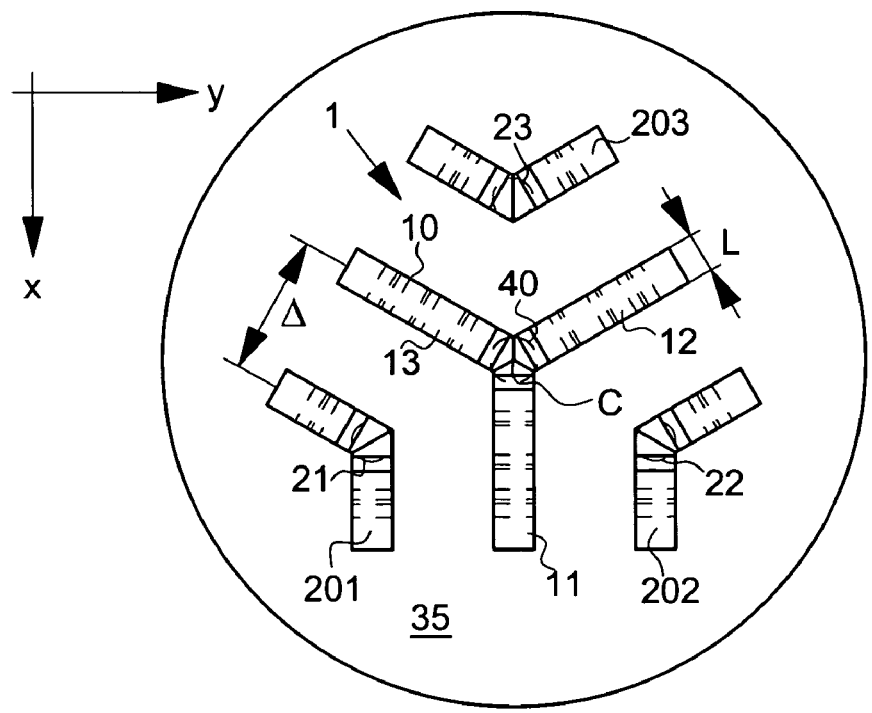
FIGS. 8 and 9 illustrate other similar variants to those of FIGS. 1 and 3, respectively, wherein the detection device is itself provided with optical guides.
Figure 9:
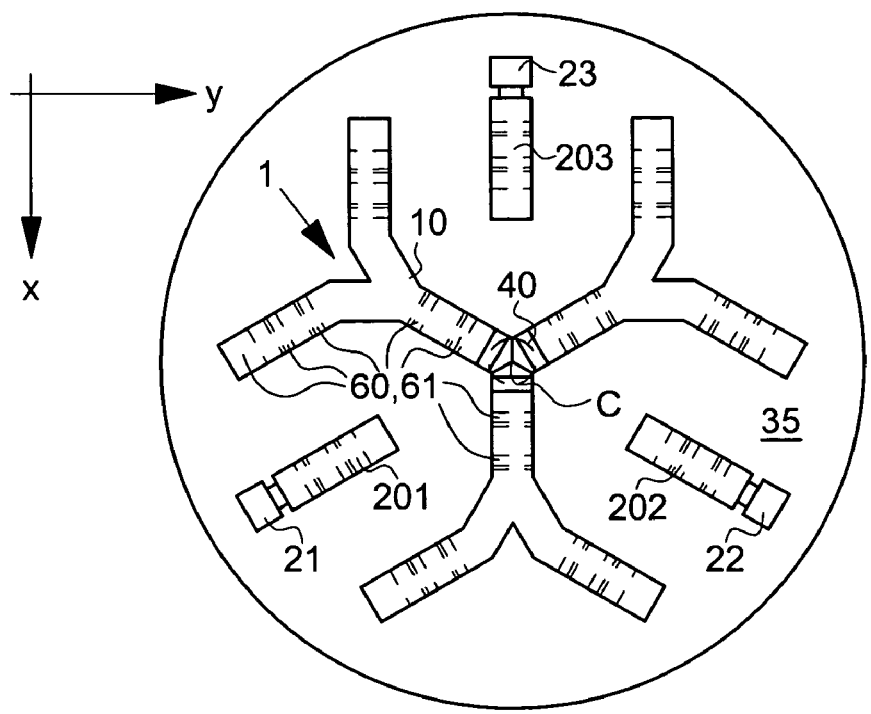

Other variants can of course be envisaged. Thus, one could envisage structuring the optical elements such that they have complementary shapes able to be fitted into each other (for example comb or spiral like structures) while still respecting a distance essentially determined between the light emission emergence zones and the light emission detection zones. FIGS. 8 and 9 show, in this regard, similar variants to those illustrated in FIGS. 1 and 3, respectively, where the three photoreceptors 21, 22, 23 are coupled to respective optical guides 201, 202 and 203. Like FIG. 7, the variant of FIG. 9 again shows that the photoreceptors can be coupled to one end of the associated optical elements.

In the illustrations of FIGS. 7, 8 and 9, it will be understood that the various optical guides of a same (illumination or detection) device could be combined in a single same optical guide and that the number of associated light sources or photoreceptors could be reduced.

Lastly, it will also be understood that several light sources emitting within distinct wavelength ranges could be simultaneously coupled on the same optical guide. In such case, it would seem wise to provide the illumination device with an optical device to mix the light emission from the various sources at the inlet of the optical element or to couple the various light sources such that their light emissions are mixed in the optical guide, the idea being above all that the light emission emerging from the various zones of the optical guide has proper uniformity and homogeneity between the various components of desired wavelengths. As already mentioned in the preamble, the use of a diffusing medium to make the optical guide would favour such homogeneity, but light intensity losses are to be expected.

Generally, it will have been understood that the use of an optical element forming a guide, such as that proposed hereinbefore, for illuminating the organic tissue and, if necessary, for detecting the light emission after propagation in the tissue, enables the available surface on the portable instrument and use of the available light energy to be optimised as far as possible.

Finally, it will be understood that various other modifications and/or improvements evident to those skilled in the art can be made to the embodiments described in the present description without departing from the scope of the invention defined by the annexed claims. In particular, the present invention is not limited solely to use in a wristwatch, but also applies to any other portable application, whether worn on the wrist or not.

What is claimed is:

1. A portable instrument, for measuring a physiological quantity, adapted to be brought into contact with a surface of an organic tissue, the portable instrument including, essentially arranged in a same plane:
   an illumination device including at least one light source with a determined illumination surface for subjecting a portion of the organic tissue to a light emission in at least one determined wavelength range; and
   a detection device distant from said illumination device for detecting intensity of the light emission produced by said illumination device after propagation in the organic tissue,
   wherein said illumination device further includes an optical element forming a guide having at least two portions at different orientations in the plane coupled to said at least one light source for guiding the light emission from said source by total internal reflection in a substantially parallel direction to the surface of the organic tissue to be illuminated and for distributing the light emission into several determined illumination zones on the surface of the organic tissue over a substantially broader area than the illumination surface of said light source.

2. The instrument according to claim 1, wherein said detection device has a determined geometrical contour and wherein each illumination zone is determined to be at a substantially constant distance from the closest point of said geometrical contour of the detection device.

3. The instrument according to claim 1, wherein said optical element forming a guide has a branched structure, or an at least partially cellular structure, or a branched and at least partially cellular structure.

4. The instrument according to claim 3, wherein said optical element forming a guide has an essentially honeycombed structure.

5. The instrument according to claim 1, wherein said detection device includes one or several quasi-punctual photoreceptors essentially arranged in the same plane as said optical element forming a guide and wherein said optical element forming a guide has a structure whose geometry essentially coincides with an arc of a circle or a circle of predetermined radius around the position of each photoreceptor.

6. The instrument according to claim 1, wherein said optical element is a solid optical guide provided with reflective micro-prismatic structures for redirecting the light emission produced by said light source in the direction of the organic tissue surface to be illuminated,
   said optical element having a first face, or lower face, directed towards said organic tissue to be illuminated, a second face, or upper face, opposite said first face, and lateral faces joining said first and second faces, oriented substantially perpendicularly to the organic tissue surface to be illuminated, each of said micro-prismatic structures including at least a first facet arranged on said second face, or on said lateral faces, or on said second face and on said lateral faces, to redirect said light emission through said first face in the direction of said organic tissue to be illuminated.

7. The instrument according to claim 6, wherein at least the first facet of each reflective micro-prismatic structure is coated with a reflective coating.

8. The instrument according to claim 6, wherein the length of said micro-prismatic structures, or the number of said micro-prismatic structures, or the length and the number of said micro-prismatic structures, increases progressively as one moves away from said light source, respectively from the associated photoreceptor, along the optical path of the light emission in said optical element.

9. The instrument according to claim 1, wherein the instrument includes a first light source for producing a light emission within a first determined wavelength range and a second light source for producing a light emission within a second determined wavelength range different from the first, said optical element forming a guide being arranged for mixing the light emissions from said first and second light sources.

10. The instrument according to claim 1, wherein said detection device includes an optical element forming a guide coupled to at least one photoreceptor for picking up in several zones of the organic tissue surface the light emission produced by the illumination device after propagation in the organic tissue and for guiding said light emission by total internal reflection towards said at least one photoreceptor.

11. A portable instruments for measuring a physiological quantity, adapted to be brought into contact with a surface of organic tissue, the portable instrument including, essentially arranged in a same plane:

an illumination device including at least one light source with a determined illumination surface for subjecting a portion of the organic tissue to a light emission in at least one determined wavelength range; and a detection device distant from said illumination device for detecting intensity of the light emission produced by said illumination device after propagation in the organic tissue, wherein said detection device includes an optical element forming a guide coupled to at least one photoreceptor for picking up in several zones of the organic tissue surface the light emission produced by the illumination device after propagation in the organic tissue and for guiding the light emission by total internal reflection to said at least one photoreceptor.

12. The instrument according to claim 11, wherein said optical element forming a guide has a branched structure, or an at least partially cellular structure, or a branched and at least partially cellular structure.

13. The instrument according to claim 12, wherein said optical element forming a guide has an essentially honeycombed structure.

14. The instrument according to claim 11, wherein said optical element is a solid optical guide provided with reflective micro-prismatic structures for redirecting the light emission emanating from the organic tissue in the direction of the associated photoreceptor or photoreceptors, said optical element having a first face, or lower face, directed towards said organic tissue from which the light emission originates, a second face, or upper face, opposite said first face, and lateral faces joining said first and second faces, oriented substantially perpendicularly to the organic tissue surface, each of said micro-prismatic structures including at least a first facet arranged on said second face, or on said lateral faces, or on said second face and on said lateral faces, to redirect said light emission emanating from the organic tissue in the direction of the associated photoreceptor or photoreceptors.

15. The instrument according to claim 14, wherein at least the first facet of each reflective micro-prismatic structure is coated with a reflective coating.

16. The instrument according to claim 14, wherein the length of said micro-prismatic structures, or the number said micro-prismatic structures, or the length and the number of said micro-prismatic structures, increases progressively as one moves away from said light source, respectively from the associated photoreceptor, along the optical path of the light emission in said optical element.

17. The instrument according to claim 11, wherein the instrument is wearable on the wrist and includes a case provided with a back cover arranged to come into contact with the user's skin and in which said illumination and detection devices are arranged.

18. A portable instrument, for measuring a physiological quantity, adapted to be brought into contact with a surface of an organic tissue, the portable instrument including, essentially arranged in a same plane:

an illumination device including at least one light source with a determined illumination surface for subjecting a portion of the organic tissue to a light emission in at least one determined wavelength range; and a detection device distant from said illumination device for detecting intensity of the light emission produced by said illumination device after propagation in the organic tissue, wherein said illumination device further includes an optical element forming a guide having at least two portions at different orientations in the plane coupled to said at least one light source for guiding the light emission from said source by total internal reflection in a substantially parallel direction to the surface of the organic tissue to be illuminated and for distributing the light emission into several determined illumination zones on the surface of the organic tissue over a substantially broader area than the illumination surface of said light source, wherein the instrument is wearable on a wrist of a user and includes a case provided with a back cover arranged to come into contact with the user's skin and in which said illumination device and detection device are arranged.

19. The instrument according to claim 18, wherein said back cover is provided with a rib intended to abut on said organic tissue to keep a space between the optical element forming a guide and the organic tissue.

20. The instrument according to claim 18, wherein at least a portion of the surface of said back cover located between the illumination and detection devices is arranged so as not to reflect the light emission produced by said illumination.

* * * * *